US00PP09508P

United States Patent [19]

Lynd

[11] Patent Number: Plant 9,508

[45] Date of Patent: Apr. 16, 1996

[54] 'FUJI-SPIKE' APPLE TREE

[75] Inventor: Andrew M. Lynd, Newark, Ohio

[73] Assignee: Lynd Fruit Farm, Inc., Pataskala, Ohio

[21] Appl. No.: 359,240

[22] Filed: Dec. 19, 1994

[51] Int. Cl.[6] ..... A01H 5/00

[52] U.S. Cl. ..... Plt./34.1

[58] Field of Search ..... Plt./34.1

[56] References Cited

PUBLICATIONS

Contreras, L., (1990) "Fuji Y Sus Mutantes" *Fruticola,* vol. 11, No. 2, p. 67.

Yoshida, Y. et al. (1981) "Studies on Improvement of Apple Breeding Techniques V Effect of Gamma Rays on Induction of Bud Sport of Fuji Variety" Bulletin of the Fruit Tree Research Station (Ministry of Agriculture, Forestry and Fisheries) Series C (Morioka), No. 8, pp. 1–14.

*Primary Examiner*—James R. Feyrer

*Attorney, Agent, or Firm*—Townsend and Townsend and Crew

[57] ABSTRACT

'Fuji-Spike' is a new variety of apple tree characterized by fruit very similar, if not identical, to the unpatented variety known as 'Fuji' but having a tree with a spur-type and semi-growth habit.

6 Drawing Sheets

DESCRIPTION

This invention relates to a new and distinctive variety of apple tree designated as 'Fuji-Spike'.

'Fuji-Spike' was found growing in a cultivated block of the variety called 'Fuji' on the Lynd Fruit Farm at 9090 Morse Road, Pataskala, Ohio. 'Fuji-Spike' is a sport mutation of 'Fuji' and was obtained from a shipment of 'Fuji' apple trees from ProTree Nursery in Brentwood, Calif. Applicant has determined that occurrence of the sport mutant in applicant's orchard was not due to contamination of the stock provided by ProTree Nursery. 'Fuji-Spike' is distinguished by its spur-type and semi-dwarf growth habit. It is similar to the 'Yataka' (U.S. Plant Pat. No. 7,001) and the 'Fuji' variety both of which produce fruit quite similar, if not identical, to 'Fuji-Spike' but neither of which displays the spur and the semi-dwarf growth habit of 'Fuji-Spike'. Additionally, 'Yataka' matures its fruit two to three weeks earlier than 'Fuji-Spike' which produces mature fruit at the same time to five days earlier than 'Fuji'.

Table "A" below compares the cross-sectional area of the tree trunk and the number of fruit spurs per foot of two year old 'Fuji-Spike' with 'Fuji', 'Yataka' and the variety known as 'Fuji Apple Tree: T.A.C. #114 Strain' (U.S. Plant Pat. No. 8,032), hereafter referred to as 'T.A.C. #114'.

TABLE "A"

| CULTIVAR | TRUNK CROSS SECTIONAL AREA[1] | NO. OF FRUIT SPURS PER FOOT OF 2 YR. WOOD |
|---|---|---|
| 'Fuji-Spike' | 28.8 SQ. IN. | 17 |
| 'Fuji' | 37.8 SQ. IN. | 7 |
| 'Yataka' | 38.3 SQ. IN. | 6 |
| 'T.A.C. #114' | N.A.[2] | 8 |

[1]Trunk cross sectional area was measured 1 foot above the ground on 5 year old trees, on M7A rootstock growing in the same field at Johnstown, OH.
[2]There were no trees of 'T.A.C. #114' growing in the same place that are the same age and rootstock as 'Fuji-Spike' for valid measurements but it appears that 'T.A.C. #114' is the same size tree as 'Fuji' and 'Yataka'.

The 'Fuji-Spike' variety is further characterized by its production of more fruit buds and apples per foot of branch than the relatively "blind" wood of both 'Fuji' and 'Yataka' which are two non-spur varieties. Also, 'Fuji-Spike' produces fewer branches resulting in a naturally open canopy requiring less pruning time to maintain a well-lighted canopy for maximum bud formation and red color development.

Table "B" below compares canopy width, height and openness of 'Fuji-Spike' with 'Fuji', 'Yataka' and 'T.A.C. #114'. The red color of 'Fuji-Spike' fruit is the same as that of 'Yataka' and 'Fuji' but is more easily obtained.

TABLE "B"

| CULTIVAR | CANOPY WIDTH | CANOPY HEIGHT | CANOPY OPENNESS |
|---|---|---|---|
| 'Fuji-Spike' | 14 FT. | 12 FT. | VERY OPEN, FEW BRANCHES |
| 'Fuji' | 14 FT. | 12 FT. | BUSHY, NOT OPEN, MANY BRANCHES |
| 'Yataka' | 14 FT. | 12 FT. | BUSHY, NOT OPEN, MANY BRANCHES |
| 'T.A.C. #114' | N.A.[1] | N.A.[1] | BUSHY, NOT OPEN, MANY BRANCHES |

[1]The 'T.A.C. #114' trees were younger than the other trees making canopy size comparisons difficult but it is estimated that 'T.A.C. #114' is virtually the same as the others.

'Fuji-Spike' produces a smaller tree than either 'Yataka' or 'Fuji' and is better adapted to orchard systems where the goals of smaller sprayers, shorter ladders and easier pruning are high priorities. This is especially important where soils and climates restrict the application of dwarfing rootstocks.

The 'Fuji-Spike' variety was asexually reproduced by chip budding 50 buds onto apple rootstock trees at The Ohio State University, Wooster, Ohio. Trees asexually reproduced from the budded trees bore identical characteristics to the original 'Fuji-Spike' tree from which the buds were taken particularly with regard to the spur-type growth habit.

IN THE DRAWINGS

DETAILED DESCRIPTION

Figure 1:
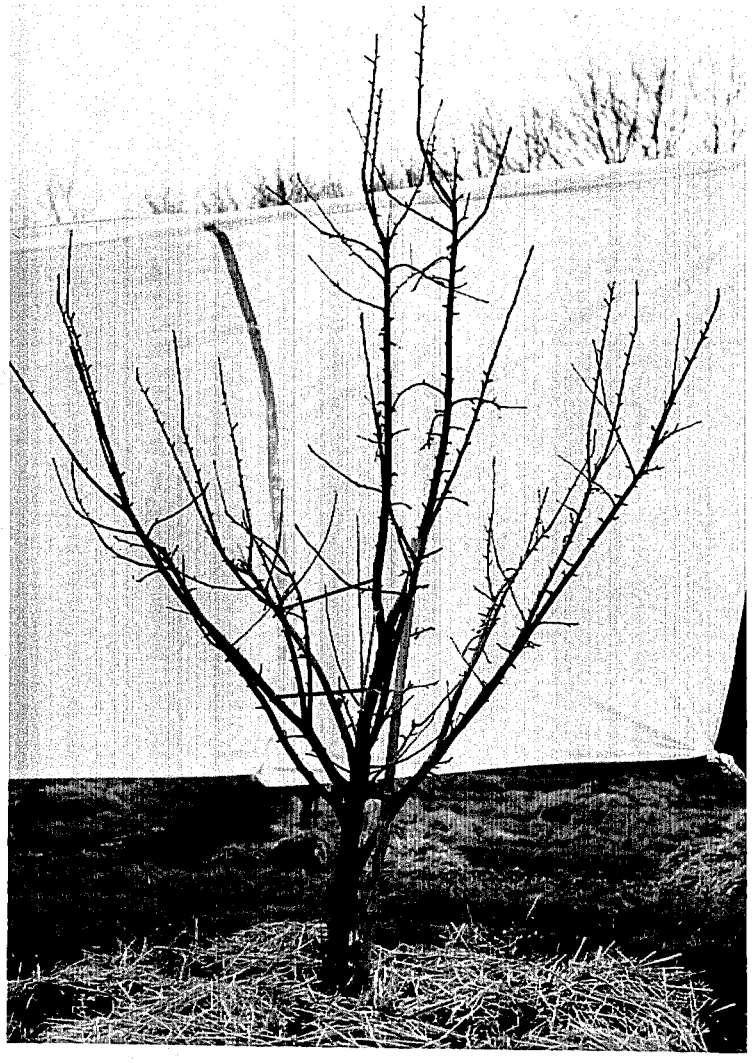
FIG. 1 depicts the original 'Fuji-Spike' apple tree.
Figure 2:
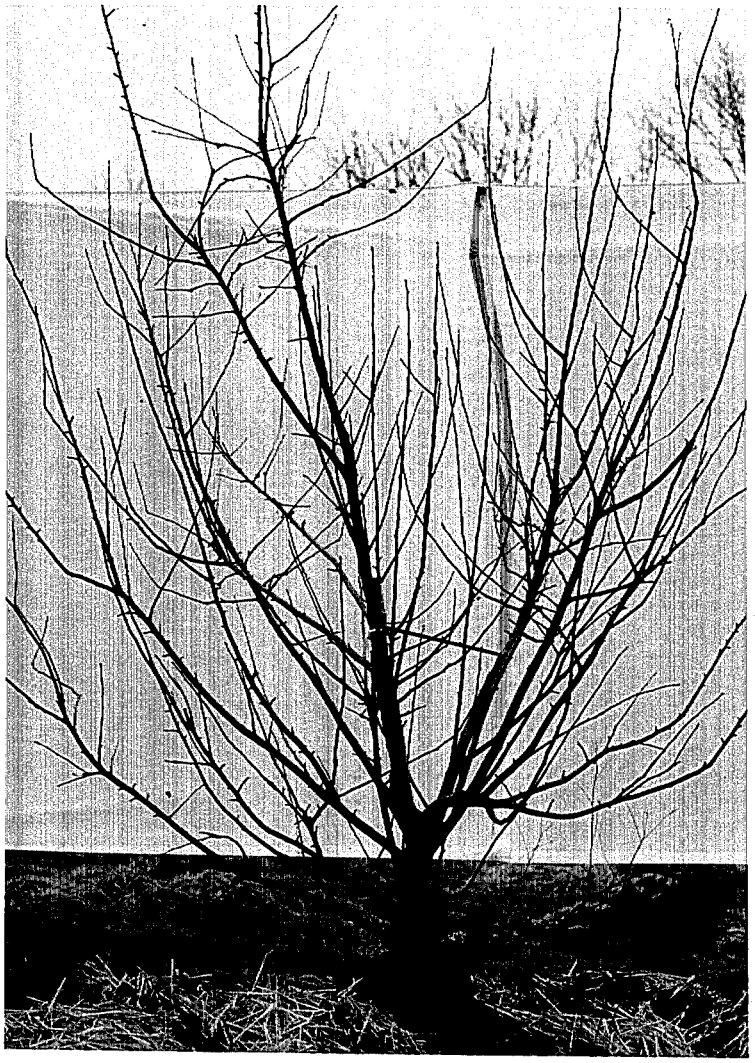
FIG. 2 depicts an apple tree typical of the 'Fuji' variety.
Figure 3:
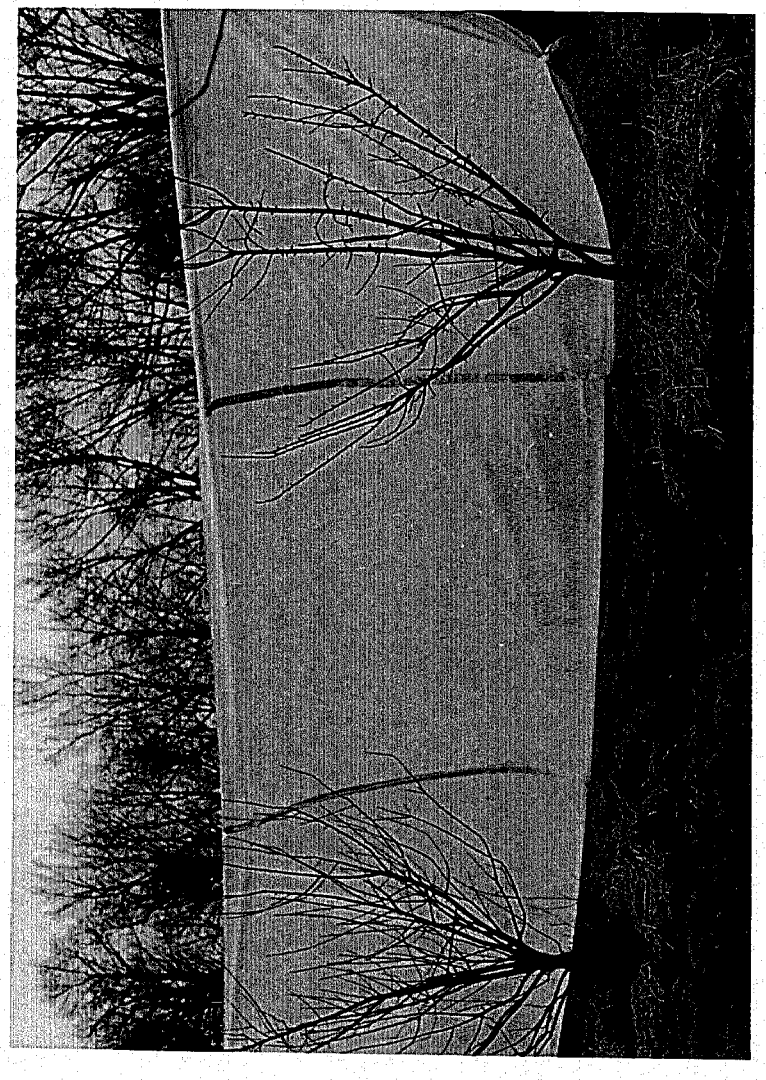
FIG. 3 illustrates trees of the 'Fuji' variety and the 'Fuji-Spike' variety growing next to each other at the Lynd Fruit Farm which were planted on the same day.
Figure 4:
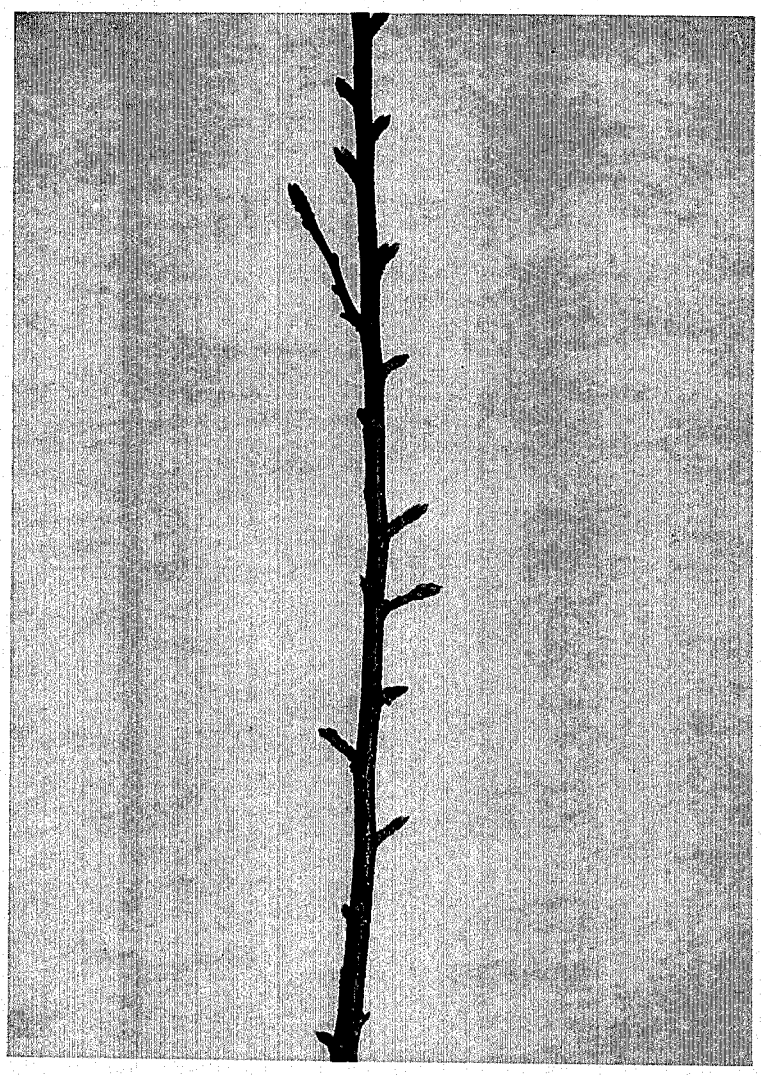
FIG. 4 shows a branch of the 'Fuji-Spike' tree of FIG. 1 and illustrates in greater detail the spur-type growth habit.
Figure 5:
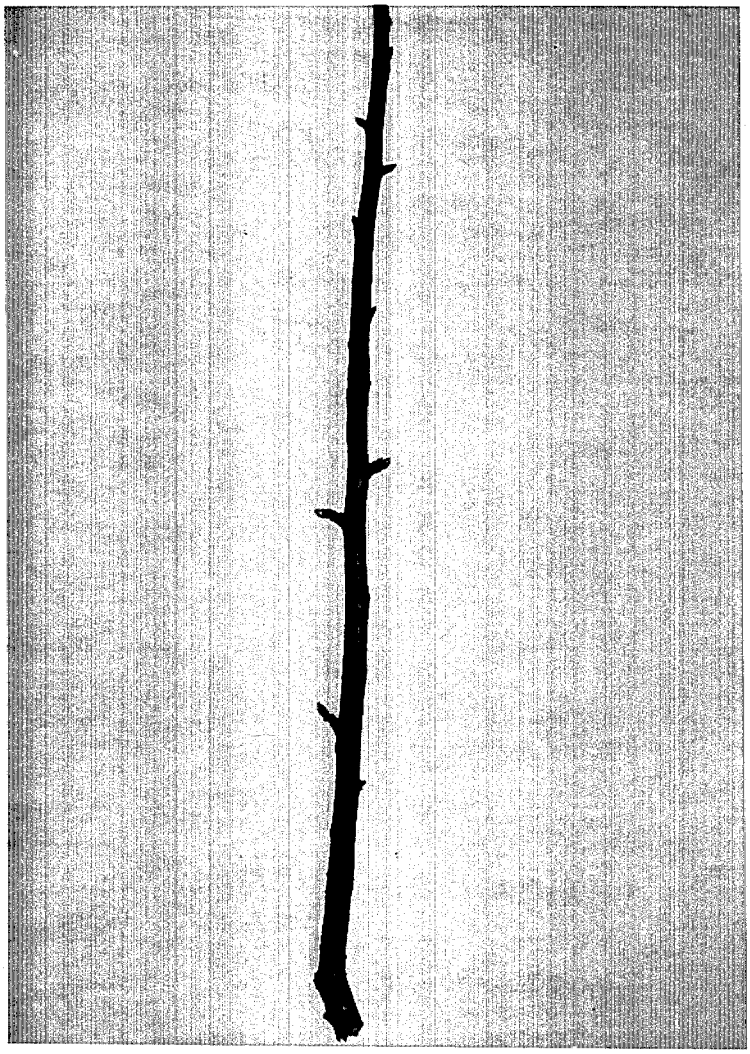
FIG. 5 illustrates a branch typical of the 'Fuji' variety shown of FIG. 2 which shows in greater detail the growth habit of the 'Fuji' variety.
Figure 6:
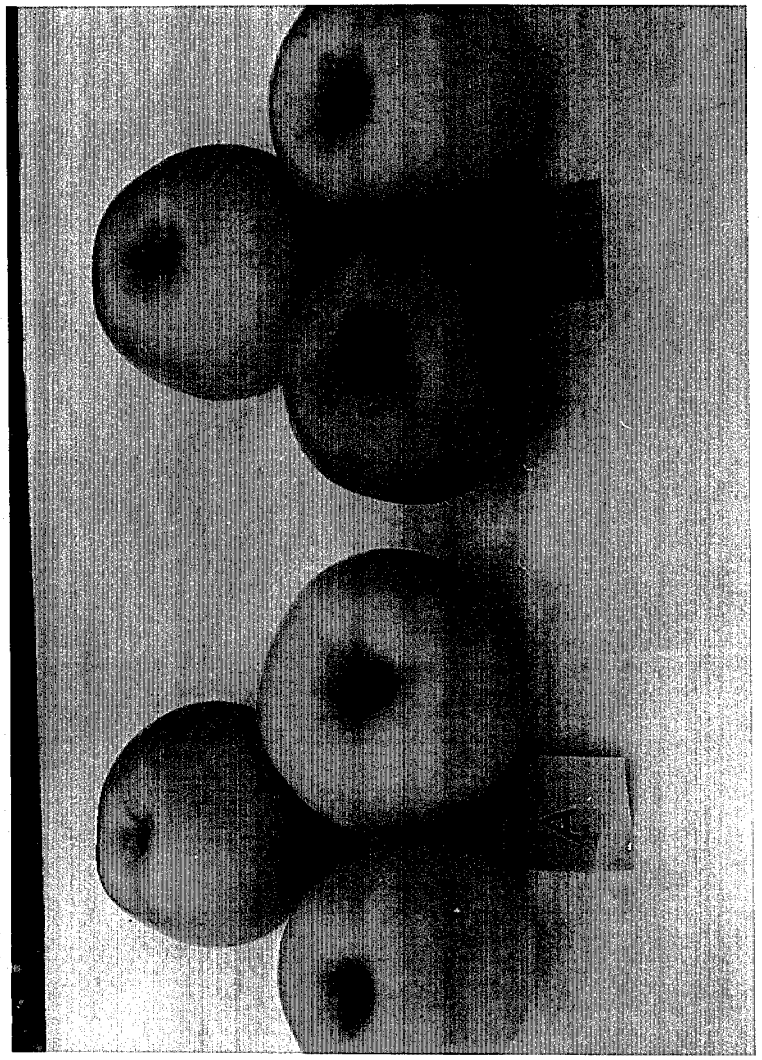
FIG. 6 illustrates three apples from the 'Fuji' tree of FIG. 2 labeled "A" and three apples from the 'Fuji-Spike' tree of FIG. 1 labeled "B". A comparison of the apples shows the similarity, if not identity, in appearance of the fruit of both varieties.

The colors identified in the detailed description are according to the Munsell Color Scale (Nickerson Color Fan).

Variety: 'Fuji-Spike'.

Origin: Whole tree sport of 'Fuji'.

Locality where grown and observed: Johnstown, Ohio, U.S.A.

Maturity date: The same to five days earlier than 'Fuji' and about 2 or 3 weeks after 'Yataka', between October 15th and 30th in central Ohio.

Tree: Medium vigor, upright, sparse-branching results in a semi-dwarf tree with very open canopy, spur-type growth habit, heavy cropping requiring only slight thinning for maximum crop size and return bloom. Tree responds to heading cuts with wide angle branching and heavy spur formation.

Trunk: Stocky, smooth, grey green to light brown in color, the same as 'T.A.C. #114'.

Shoots: Dormant shoot is brown (Munsell 5YR2/4) and thick with small, whitish, round to slightly oval lenticels which become more numerous, more conspicuous, raised and whiter on two year old wood. Pubescence on dormant one year old wood is very slight with medium internodal length.

Leaf:

*Blade.*—Medium to medium large, moderate folding, midrib slightly reflexed, edges waved, oval to ovate, with rather upright angle to the branch.

*Serrations.*—Moderately sharp, rather coarse, quite regular, uniform, and distinct.

*Surface.*—Intermediate between dull and shiny on the upper surface with a slight pubescence on underside. Texture of upper surface is more rough than smooth. Noticeably darker green than 'T.A.C. #114' and 'Yataka'. Leaf length is 85 to 90 mm, width is 55–60 mm, petiole is short, 15 to 18 mm, tip is sharply pointed, bracts prominent, borne in pairs, opposite, narrow, pointed, borne 3–4 mm from abscision zone, identical to 'T.A.C. #114'.

Flowers: Flowers not atypical; bloom midseason from May 1 to May 10 at Licking county, Ohio.

*Size.*—Medium.

*Color.*—White.

*Stamens.*—Single row, anthers flesh, yellow, turning dark brown with pollen shed.

*Pistil.*—Stigmas; broad, flat at top, rounded at base.

*Styles.*—Medium long, fused at base.

*Sepals.13* Medium size, pubescent.

Pollination requirements: Satisfied by other diploid strains such as 'Golden Delicious', 'Winder Banana', and commonly used strains of crab apples.

Fruit:

*Size.*—Medium (250 grams) to large (350 grams). Vertical Circumference is 26 cm; Horizontal Circumference is 26 cm. *Shape.*—Rounded, slightly longer than wide and fairly uniform when small fruit is thinned off. If not removed, some smaller fruit will be wider than long giving a flatter look and oftentimes slightly oval shaped. Internal fruit and flesh characteristics are identical to 'Yataka'. Both stem and blossom ends are uniformly curved and rounded.

*Cavity.*—Deep and wide.

*Calyx.*—Closed.

*Core.*—Axis of core is perpendicular to fruit body.

*Color.*—Up to five days earlier than 'Fuji', not due to increased fruit exposure to the sun. Slightly darker and more solid than 'Fuji', but not strikingly different.

Carpels and seeds: Identical to those of 'Fuji'.

Basin: Medium depth and breadth.

Storage: Storage life is extremely long, up to 6 months under refrigeration and 12 months under controlled atmosphere. Fruit remains crisp at room temperature much longer than most apples.

I claim:

1. The new and distinct variety of apple tree illustrated and described and having the characteristics above enumerated.

* * * * *